United States Patent
Yamakawa et al.

(10) Patent No.: US 10,180,392 B2
(45) Date of Patent: *Jan. 15, 2019

(54) PLASMA PROCESSING DETECTION INDICATOR USING INORGANIC SUBSTANCE AS A COLOR-CHANGE LAYER

(71) Applicant: SAKURA COLOR PRODUCTS CORPORATION, Osaka-shi, Osaka (JP)

(72) Inventors: Yu Yamakawa, Osaka (JP); Kazuhiro Uneyama, Osaka (JP); Keita Hishikawa, Osaka (JP); Masayuki Nishi, Kyoto (JP); Masahiro Shimizu, Kyoto (JP)

(73) Assignee: SAKURA COLOR PRODUCTS CORPORATION, Osaka-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/309,510

(22) PCT Filed: Apr. 22, 2015

(86) PCT No.: PCT/JP2015/062244
§ 371 (c)(1),
(2) Date: Nov. 8, 2016

(87) PCT Pub. No.: WO2015/170592
PCT Pub. Date: Nov. 12, 2015

(65) Prior Publication Data
US 2017/0153174 A1    Jun. 1, 2017

(30) Foreign Application Priority Data
May 9, 2014    (JP) ................... 2014-097321

(51) Int. Cl.
*G01N 21/78* (2006.01)
*G01N 31/22* (2006.01)
(Continued)

(52) U.S. Cl.
CPC .......... *G01N 21/255* (2013.01); *C01G 29/00* (2013.01); *C01G 31/02* (2013.01); *C01G 39/02* (2013.01);
(Continued)

(58) Field of Classification Search
CPC .... G01N 21/78; G01N 31/226; G01N 31/223; G01N 21/718; G01N 21/75;
(Continued)

(56) References Cited

U.S. PATENT DOCUMENTS

| 3,568,627 A | 3/1971 | Selinger et al. |
| 4,155,895 A | 5/1979 | Rohowetz et al. |

(Continued)

FOREIGN PATENT DOCUMENTS

| CN | 1877777 A | 12/2006 |
| CN | 101014668 A | 8/2007 |

(Continued)

OTHER PUBLICATIONS

International Search Report dated Jul. 14, 2015, issued in counterpart application No. PCT/JP2015/062244. (2 pages).
(Continued)

*Primary Examiner* — Jennifer Wecker
(74) *Attorney, Agent, or Firm* — Westerman, Hattori, Daniels & Adrian, LLP

(57) ABSTRACT

The present invention provides a plasma treatment detection indicator including a color-changing layer that changes color by plasma treatment, exhibiting excellent heat resistance, with the gasification of the color-changing layer or the scattering of the fine debris of the color-changing layer (Continued)

caused by the plasma treatment being suppressed to such a degree as to not affect the electronic device properties. Specifically, the present invention provides a plasma treatment detection indicator including a color-changing layer that changes color by plasma treatment, the color-changing layer containing at least one metal element selected from the group consisting of Mo, W, Sn, V, Ce, Te, and Bi in the form of a simple substance and/or an inorganic compound containing at least one metal element selected from the group consisting of Mo, W, Sn, V, Ce, Te, and Bi.

12 Claims, 1 Drawing Sheet

(51) Int. Cl.
| | | |
|---|---|---|
| C01G 29/00 | (2006.01) | |
| C01G 31/02 | (2006.01) | |
| C01G 39/02 | (2006.01) | |
| C01G 41/02 | (2006.01) | |
| G01N 21/25 | (2006.01) | |
| H01L 21/3065 | (2006.01) | |
| C23C 16/50 | (2006.01) | |
| C23C 16/52 | (2006.01) | |
| G01N 21/75 | (2006.01) | |
| C04B 35/453 | (2006.01) | |
| C04B 35/495 | (2006.01) | |
| C23C 24/00 | (2006.01) | |
| H01J 37/32 | (2006.01) | |
| H01L 21/67 | (2006.01) | |
| H01J 37/244 | (2006.01) | |
| G01N 21/71 | (2006.01) | |
| H01L 21/3213 | (2006.01) | |

(52) U.S. Cl.
CPC .......... *C01G 41/02* (2013.01); *C04B 35/453* (2013.01); *C04B 35/495* (2013.01); *C23C 16/50* (2013.01); *C23C 16/52* (2013.01); *C23C 24/00* (2013.01); *G01N 21/75* (2013.01); *G01N 21/78* (2013.01); *G01N 31/22* (2013.01); *G01N 31/223* (2013.01); *G01N 31/226* (2013.01); *H01J 37/32935* (2013.01); *H01L 21/3065* (2013.01); *C01P 2006/60* (2013.01); *C04B 2235/3239* (2013.01); *C04B 2235/3256* (2013.01); *C04B 2235/3258* (2013.01); *C04B 2235/3298* (2013.01); *C04B 2235/5436* (2013.01); *G01N 21/718* (2013.01); *H01J 37/32449* (2013.01); *H01J 37/32541* (2013.01); *H01J 2237/3321* (2013.01); *H01J 2237/3341* (2013.01); *H01L 21/32136* (2013.01)

(58) Field of Classification Search
CPC .......... H01L 21/32136; H01L 21/3065; C01G 29/00; C01G 31/02; C01G 39/02; C01G 41/02; C23C 16/50; C23C 16/52
See application file for complete search history.

(56) References Cited

U.S. PATENT DOCUMENTS

| | | |
|---|---|---|
| 4,179,397 A | 12/1979 | Rohowetz et al. |
| 4,448,548 A | 5/1984 | Foley |
| 4,839,311 A | 6/1989 | Riley et al. |
| 5,955,025 A | 9/1999 | Barrett |
| 5,990,199 A | 11/1999 | Bealing et al. |
| 6,063,631 A | 5/2000 | Ignacio |
| 6,117,685 A | 9/2000 | Omatsu et al. |
| 6,238,623 B1 | 5/2001 | Amhof et al. |
| 6,267,242 B1 | 7/2001 | Nagata et al. |
| 6,355,448 B1 | 3/2002 | Foltz et al. |
| 6,410,338 B1 | 6/2002 | Lippold et al. |
| 6,524,763 B1 | 2/2003 | Kuroda et al. |
| 6,659,036 B2 | 12/2003 | Omatsu et al. |
| 6,852,281 B2 | 2/2005 | Inoue et al. |
| 7,189,355 B2 | 3/2007 | Mikumo et al. |
| 7,213,534 B2 | 5/2007 | Siikaluoma et al. |
| 7,364,700 B2 | 4/2008 | Maruo et al. |
| 7,364,770 B2 | 4/2008 | Nagashima et al. |
| 7,976,781 B2 | 7/2011 | Maruo et al. |
| 7,981,687 B2 | 7/2011 | Yamaguchi et al. |
| 8,222,327 B2 | 7/2012 | Mikumo et al. |
| 8,343,437 B2 | 1/2013 | Patel |
| 8,530,242 B2 | 9/2013 | Lin et al. |
| 8,567,338 B2 | 10/2013 | Greene et al. |
| 9,168,086 B2 | 10/2015 | Allen |
| 9,194,808 B2 | 11/2015 | Yamaguchi et al. |
| 9,944,061 B2 | 4/2018 | Garhart |
| 2001/0054374 A1 | 12/2001 | Omatsu et al. |
| 2002/0051733 A1 | 5/2002 | Antonoplos et al. |
| 2002/0121629 A1 | 9/2002 | Mikumo et al. |
| 2005/0054374 A1 | 3/2005 | Namiki |
| 2006/0194056 A1 | 8/2006 | Nagashima et al. |
| 2006/0244379 A1 | 11/2006 | Shin |
| 2006/0283746 A1 | 12/2006 | Sutoh et al. |
| 2008/0090726 A1 | 4/2008 | Eskra et al. |
| 2008/0267811 A1* | 10/2008 | Yamaguchi .......... G01N 31/223 422/3 |
| 2009/0212237 A1 | 8/2009 | Sugiki et al. |
| 2010/0119410 A1 | 5/2010 | Yamaguchi et al. |
| 2011/0009535 A1 | 1/2011 | Mikumo et al. |
| 2011/0065203 A1 | 3/2011 | Studer et al. |
| 2011/0275159 A1* | 11/2011 | Landgrebe .............. A61L 2/28 436/1 |
| 2011/0312096 A1* | 12/2011 | Whitman ............. G01N 31/226 436/1 |
| 2012/0100395 A1 | 4/2012 | Feller et al. |
| 2012/0315659 A1 | 12/2012 | Andreescu et al. |
| 2014/0154808 A1* | 6/2014 | Patel ..................... G01K 3/04 436/1 |
| 2015/0050745 A1* | 2/2015 | Karato ................ G01N 31/226 436/135 |
| 2016/0045631 A1 | 2/2016 | Yamaguchi et al. |
| 2016/0133444 A1 | 5/2016 | Oshiro et al. |
| 2016/0141192 A1 | 5/2016 | Uneyama et al. |
| 2016/0349222 A1 | 12/2016 | Mori |
| 2017/0044389 A1 | 2/2017 | Mori |
| 2017/0101548 A1 | 4/2017 | Mori et al. |
| 2017/0153174 A1 | 6/2017 | Yamakawa et al. |
| 2017/0261476 A1 | 9/2017 | Hishikawa et al. |
| 2017/0330777 A1 | 11/2017 | Hishikawa et al. |

FOREIGN PATENT DOCUMENTS

| | | |
|---|---|---|
| EP | 1312918 A2 | 5/2003 |
| GB | 2 168 082 A | 6/1986 |
| JP | 63-36786 A | 2/1988 |
| JP | S63-36876 A | 2/1988 |
| JP | 1-295423 A | 11/1989 |
| JP | 4-305492 A | 10/1992 |
| JP | 6-69165 A | 3/1994 |
| JP | 7-26477 A | 1/1995 |
| JP | 11-37988 A | 2/1999 |
| JP | 2000-269191 A | 9/2000 |
| JP | 2001-174449 A | 6/2001 |
| JP | 2001-237097 A | 8/2001 |
| JP | 2001-242249 A | 9/2001 |
| JP | 2002-011081 A | 1/2002 |
| JP | 2002-022534 A | 1/2002 |
| JP | 2002-502953 A | 1/2002 |
| JP | 2002-303618 A | 10/2002 |
| JP | 2002/322315 A | 11/2002 |
| JP | 2002-323451 A | 11/2002 |
| JP | 2003-506156 A | 2/2003 |
| JP | 2003-515744 A | 5/2003 |
| JP | 2003-325646 A | 11/2003 |

(56) References Cited

FOREIGN PATENT DOCUMENTS

| | | | |
|---|---|---|---|
| JP | 2004-101488 A | 4/2004 |
| JP | 2004-146738 A | 5/2004 |
| JP | 2004-146739 A | 5/2004 |
| JP | 2004-203984 A | 7/2004 |
| JP | 2004-298479 A | 10/2004 |
| JP | 2005111154 A | 4/2005 |
| JP | 2005-142287 A | 6/2005 |
| JP | 2005-315828 A | 11/2005 |
| JP | 2005-329019 A | 12/2005 |
| JP | 2006-78463 A | 3/2006 |
| JP | 2006-223351 A | 8/2006 |
| JP | 2007-40785 A | 2/2007 |
| JP | 2008-125760 A | 6/2008 |
| JP | 2009-213609 A | 9/2009 |
| JP | 2010-501655 A | 1/2010 |
| JP | 2011-530085 A | 12/2011 |
| JP | 2012-050664 A | 3/2012 |
| JP | 2012-068811 A | 4/2012 |
| JP | 2012-78202 A | 4/2012 |
| JP | 2013-095764 A | 5/2013 |
| JP | 2013-95765 A | 5/2013 |
| JP | 2013-98196 A | 5/2013 |
| JP | 2013098196 A | * 5/2013 |
| JP | 2013-233387 A | 11/2013 |
| JP | 2014-109523 A | 6/2014 |
| JP | 2016-111063 A | 6/2016 |
| WO | 98/46279 A1 | 10/1998 |
| WO | 98/46994 A1 | 10/1998 |
| WO | 99/39754 A1 | 8/1999 |
| WO | 01/10476 A1 | 2/2001 |
| WO | 01/40792 A1 | 6/2001 |
| WO | 2004-087222 A1 | 10/2004 |
| WO | 2006/109726 A1 | 10/2006 |
| WO | 2008/022952 A1 | 2/2008 |
| WO | 2013/129473 A1 | 9/2013 |
| WO | 2014/038612 A1 | 3/2014 |
| WO | 2014/196440 A1 | 12/2014 |
| WO | 2015/025699 A1 | 2/2015 |
| WO | 2015/170592 A1 | 11/2015 |

OTHER PUBLICATIONS

International Search Report dated Apr. 14, 2015, issued in counterpart International Application No. PCT/JP2015/053742 (1 page).
Masaaki Nagatsu, Plasma Sterilization, Journal of Plasma and Fusion Research, 2007, vol. 83, No. 7, pp. 601-606.
Notice of Allowance dated Nov. 22, 2017, issued in U.S. Appl. No. 15/316,980 (15 pages).
Final Office Action dated Nov. 17, 2017, issued in U.S. Appl. No. 14/895,835 (18 pages).
International Search Report dated Sep. 2, 2014, issued in Application No. PCT/JP2014/064209 (4 pages).
English translation of Written Opinion dated Nov. 17, 2015, issued in counterpart Application No. PCT/JP2015/073769 (4 pages).
International Search Report dated Nov. 17, 2015, issued in Application No. PCT/JP2015/073769 (3 pages).
Non-Final OA dated Jun. 28, 2017, issued in U.S. Appl. No. 14/895,835 (19 pages).
Non-Final OA dated Jun. 30, 2017, issued in U.S. Appl. No. 15/316,980 (20 pages).
International Search Report dated Jul. 14, 2015, issued in counterpart International Application No. PCT/JP2015/061545 (4 pages).
Non-Final OA dated Jul. 3, 2017, issued in U.S. Appl. No. 15/305,822 (11 pages).
International Search Report dated Feb. 9, 2016, issued in counterpart Application No. PCT/JP2015/082841 (2 pages).
International Search Report dated Sep. 16, 2014, issued in counterpart Application No. PCT/JP2014/070419 (2 pages).
Office Action dated Mar. 14, 2017, issued in Chinese Application No. 201480033301.2, with partial English translation (11 pages).
Office Action dated Jun. 9, 2010, issued in counterpart Japanese Application No. 2005-064179 (2 pages).
International Search Report dated May 17, 2005, issued in Application No. PCT/JP2005/006138 (1 page).
Non-Final Office Action dated Mar. 4, 2009, issued in U.S. Appl. No. 10/594,587 (9 pages).
Final Office Action dated Nov. 27, 2009, issued in U.S. Appl. No. 10/594,587 (11 pages).
Non-Final OA dated Jun. 11, 2010, issued in U.S. Appl. No. 10/594,587 (6 pages).
Final Office Action dated Dec. 23, 2010, issued in U.S. Appl. No. 10/594,587 (5 pages).
Notice of Allowance dated Apr. 1, 2011, issued in U.S. Appl. No. 10/594,587 (7 pages).
Final Office Action dated Nov. 17, 2017, issued in U.S. Appl. No. 15/305,822 (9 pages).
Non-Final Office Action dated Jan. 31, 2018, issued in U.S. Appl. No. 15/529,382 (25 Pages).
Non-Final Office Action dated Nov. 20, 2017, issued in U.S. Appl. No. 14/897,461 (27 pages).
Non-Final Office Action dated Mar. 1, 2018, issued in U.S. Appl. No. 15/305,822 (7 pages).
Notice of Allowance dated Mar. 22, 2018, issued in U.S. Appl. No. 15/316,980 (18 pages).
English Translation of JP20021303618, dated Oct. 2002; (14 pages) cited in Non-Final Office Action dated Mar. 1, 2018 for U.S. Appl. No. 15/305,822.
English Translation of JP 2004/101488, dated Apr. 2004 (9 pages) cited in Non-Final Office Action dated Mar. 1, 2018 for U.S. Appl. No. 15/305,822.
English Translation of WO 2014/038612, dated Mar. 2014 (10 pages) cited in Non-Final Office Action dated Mar. 1, 2018 for U.S. Appl. No. 15/305,822.
Janus Green B, no date available; https://pubchem.ncbi.nlm.nih.gov/compound/Janus_green_B (17 pages) cited in Non-Final Office Action dated Mar. 1, 2018 for U.S. Appl. No. 15/305,822.
Bakelite BKUA 2370, Georgia Pacific Chemicals Phenolic Resins, no date available, http://www.brenntag.com/specialties/en/product-industries/industries/material-science/composites-and-advanced-materials/georgia-pacific-phenolic-resins-dispersions-composites.jsp (3 pages) cited in Non-Final Office Action dated Mar. 1, 2018 for U.S. Appl. No. 15/305,822.
Sylowhite SM 405, Jul. 2009, http://novana.ch/news/8/3/0/sylowhite-sm-405 (1 page) cited in Non-Final Office Action dated Mar. 1, 2018 for U.S. Appl. No. 15/305,822.
Final Office Action dated Nov. 17, 2017, issued in U.S. Appl. No. 15/305,822, (13 pages).
Non-Final Office Action dated May 17, 2018, issued in U.S. Appl. No. 15/117,601 (28 pages).
Office Action dated Mar. 20, 2018, issued in counterpart Japanese Application No. 2014-087638, with English translation (9 pages).
Office Action dated Sep. 28, 2010, issued in counterpart Japanese Application No. 2005-064179, with English translation (5 pages).
Office Action dated Mar. 26, 2013, issued in counterpart Japanese Application No. 2010-263654, with English translation (5 pages).
Notice of Allowance dated Jun. 13, 2018, issued in U.S. Appl. No. 15/316,980 (19 pages).
Notice of Allowance dated Aug. 7, 2018, issued in U.S. Appl. No. 15/305,822 (18 pages).
Notice of Allowance dated Aug. 15, 2018, issued in U.S. Appl. No. 15/529,382 (16 pages).
Kitaoka, Kyozo, "Guide for Coatings to Synthetic Resin", May 25, 1974, First Edition, pp. 212-213, with English translation; Cited in Japanese Office Action dated Aug. 21, 2018.
"Toryo Genryo Binran [Paint Material Handbook]", Japan Paint Manufacturers Association, May 31, 1999, 7th Edition, pp. 77-79, with English translation; Cited in Japanese Office Action dated Aug. 21, 2018.
Office Action dated Aug. 21, 2018, issued in Japanese Application No. 2014-087638, with English translation (7 pages).
Office Action dated Aug. 28, 2018, issued in counterpart Japanese Application No. 2015-532792, with English translation (6 pages).
Office Action dated Sep. 5, 2018, issued in counterpart Chinese Application No. 201580020478.3, with English translation (12 pages).

(56) References Cited

OTHER PUBLICATIONS

Office Action dated Oct. 9, 2018, issued in counterpart Japanese Application No. 2015-562838, with English translation (5 pages).
Office Action dated Oct. 9, 2018, issued in counterpart Japanese Application No. 2014-244414, with English translation (7 pages).
Final Office Action dated Sep. 20, 2018, issued in U.S. Appl. No. 15/117,601 (21 pages).
Final Office Action dated Oct. 29, 2018, issued in U.S. Appl. No. 15/117,601 (15 pages).
Office Action dated Dec. 4, 2018, issued in counterpart Japanese Application No. 2015-095244, with English translation (5 pages).

* cited by examiner

PLASMA PROCESSING DETECTION INDICATOR USING INORGANIC SUBSTANCE AS A COLOR-CHANGE LAYER

TECHNICAL FIELD

The present invention relates to a plasma treatment detection indicator in which an inorganic substance is used as a color-changing layer, the indicator being useful as an indicator particularly for use in electronic device production equipment.

BACKGROUND ART

In the production process of electronic devices, a variety of treatments are typically performed on the electronic device substrate (substrate to be treated). In the case of, for example, a semiconductor as the electronic device, a semiconductor wafer (wafer) is loaded; after that, a film forming step of forming an insulating film or a metal film, a photolithography step of forming a photoresist pattern, an etching step of processing the film using the photoresist pattern, an impurity-adding step of forming a conductive layer on the semiconductor wafer (also called doping or diffusion process), a CMP step of polishing the uneven surface of the film to flatten the surface (chemical mechanical planarization), and the like are performed, followed by semiconductor wafer electrical characteristics inspection for inspecting the finish of the pattern or the electrical characteristics (these steps may be collectively referred to as the front-end process). Subsequently, the back-end process of forming semiconductor chips follows. This front-end process is also performed not only when the electronic device is a semiconductor, but also when other electronic devices (e.g., light-emitting diodes (LED), solar batteries, liquid crystal displays, and organic EL (Electro-Luminescence) displays) are produced.

The front-end process includes, in addition to the steps described above, a washing step using plasma, ozone, ultraviolet rays, and the like, and a step of removing a photoresist pattern using plasma, radical containing gas, and the like (also called ashing or ash removal). The film-forming step also includes CVD for forming a film by chemically reacting a reactive gas on the wafer surface, and sputtering for forming a metal film. The etching step includes dry etching performed by chemical reaction in plasma, and etching by ion beams. The "plasma" refers to the state in which gas is dissociated, and ions, radicals, and electrons are present in the plasma.

In the production process of electronic devices, the various treatments described above must be properly performed to secure the performance, reliability, and the like of electronic devices. Thus, in the plasma treatment represented by a film-forming step, an etching step, an ashing step, an impurity-adding step, a washing step, etc., a completion check and the like is performed to confirm the completion of the plasma treatment, for example, by emission analysis of plasma with a spectrometer, and a plasma treatment detection indicator comprising a color-changing layer that changes color in a plasma treatment atmosphere.

As an example of the plasma treatment detection indicator, Patent Literature 1 discloses an ink composition for detecting plasma treatment comprising 1) at least one of anthraquinone colorants, azo colorants, or phthalocyanine colorants; and 2) at least one of binder resins, cationic surfactants, or extenders, wherein a plasma-generating gas used in the plasma treatment contains at least one of oxygen or nitrogen. Patent Literature 1 also discloses a plasma treatment detection indicator comprising a color-changing layer that comprises the ink composition formed on a base material.

Patent Literature 2 discloses an ink Composition for detecting inert gas plasma treatment, comprising (1) at least one of anthraquinone colorants, azo colorants, and methine colorants; and (2) at least one of binder resins, cationic surfactants and extenders, the inert gas containing at least one selected from the group consisting of helium, neon, argon, krypton, and xenon. Patent Literature 2 also discloses a plasma treatment detection indicator in which a color-changing layer comprising the ink composition is formed on a base material.

However, the check method using emission analysis or a traditional plasma treatment detection indicator may be insufficient in performance as an indicator for use in electronic device production equipment. Specifically, because of the limitation to the measurement and analysis performed through the window provided to the electronic device production equipment, it tends to be difficult to perform efficient measurement or analysis with the check method using emission analysis when the inside of the electronic device production equipment cannot be seen. Although the use of the traditional plasma treatment detection indicator is a convenient and excellent means for confirming the completion of plasma treatment through the color change of the color-changing layer, the organic components contained in the color-changing layer, such as a colorant, a binder resin, and a surfactant, may possibly lead to decreased cleanliness of the electronic device production equipment, or contamination of electronic devices due to the gasification of organic components or scattering of the fine debris of organic components caused by plasma treatment. The gasification of organic components may adversely affect the vacuum performance of the electronic device production equipment. In addition, because of the insufficient heat resistance of the traditional color-changing layer composed primarily of organic components, it is difficult to use it as an indicator when the electronic device production equipment has a high temperature.

Therefore, there has been a demand for the development of a plasma treatment detection indicator comprising a color-changing layer that changes color by plasma treatment, exhibiting excellent heat resistance with the gasification of the color-changing layer or the scattering of the fine debris of the color-changing layer caused by the plasma treatment being suppressed to such a degree as to not affect the electronic device properties.

CITATION LIST

Patent Literature

Patent Literature 1: JP2013-98196
Patent Literature 2: JP2013-95764

SUMMARY OF INVENTION

Technical Problem

An object of the present invention is to provide a plasma treatment detection indicator comprising a color-changing layer that changes color by plasma treatment, exhibiting excellent heat resistance with the gasification of the color-changing layer or the scattering of the fine debris of the color-changing layer caused by the plasma treatment being suppressed to such a degree as to not affect the electronic device properties.

Solution to Problem

The present inventors conducted extensive research to achieve the object, and found that the use of a specific metal element in the form of a simple substance and/or an inorganic compound containing the metal element as a color-changing material to be contained in a color-changing layer can achieve the object. The inventors then completed the present invention.

Specifically, the present invention relates to the following plasma treatment detection indicator.

Item 1. A plasma treatment detection indicator comprising a color-changing layer that changes color by plasma treatment, the color-changing layer comprising at least one metal element selected from the group consisting of Mo, W, Sn, V, Ce, Te, and Bi in the form of a simple substance and/or an inorganic compound containing at least one metal element selected from the group consisting of Mo, W, Sn, V, Ce, Te, and Bi.

Item 2. The plasma treatment detection indicator according to item 1, wherein the valence of the at least one metal element contained in the inorganic compound is at least one member selected from the group consisting of Mo(II) to Mo (VI), W(II) to W(VI), Sn(II), Sn(IV), V(II) to V(V), Ce(III) to Ce(IV), Te(II), Te(IV), Te(VI), Bi(III), and Bi (V).

Item 3. The plasma treatment detection indicator according to Item 1 or 2, wherein the inorganic compound is at least one member selected from the group consisting of oxides, hydroxides, carbonates, oxide salts, oxoacids, oxoacid salts, and oxo complexes of the least one metal element.

Item 4. The plasma treatment detection indicator according to any one of items 1 to 3, wherein the color-changing layer comprises at least one member selected from the group consisting of molybdenum(IV) oxide, molybdenum (VI) oxide, tungsten(VI) oxide, tin(IV) oxide, vanadium (II) oxide, vanadium (III) oxide, vanadium(IV) oxide, vanadium(V) oxide, cerium(IV) oxide, tellurium(IV) oxide, bismuth (III) oxide, cerium(IV) hydroxide, bismuth (III) hydroxide, vanadium(III) hydroxide, molybdenum (V)) hydroxide, bismuth(III) carbonate oxide, vanadium(IV) oxide sulfate, ammonium molybdate, sodium molybdate, potassium molybdate, sodium tungstate, ammonium tungstate, sodium orthovanadate, ammonium metavanadate, and sodium metavanadate.

Item 5. The plasma treatment detection indicator according to any one of items 1 to 3, wherein the color-changing layer comrises at least one member selected from the group consisting of molybdenum(VI) oxide, tungsten (VI) oxide, vanadium (III) oxide, vanadium (V) oxide, and bismuth(III) oxide.

Item 6. The plasma treatment detection indicator according to any one of items 1 to 5, comprising a base material that supports the color-changing layer.

Item 7. The plasma treatment detection indicator according any one of items 1 to 6, which is an indicator for use in electronic device production equipment.

Item 8. The plasma treatment detection indicator according to item 7, wherein the shape of the indicator is identical to the shape of an electronic device substrate for use in the electronic device production equipment.

Item 9. The plasma treatment detection indicator according to item 7 or 8, wherein the electronic device production equipment performs at least one plasma treatment selected from the group consisting of film-forming step, etching step, asking step, impurity-adding step, and washing step.

Item 10. The plasma treatment detection indicator according any one of items 1 to 9, comprising a non-color-changing layer that does not change color by plasma treatment.

Item 11. The plasma treatment detection indicator according to item 10, wherein the non-color-changing layer comprises at least one member selected from the group consisting of titanium(IV) oxide, zirconium(IV) oxide, yttrium(III) oxide, barium sulfate, magnesium oxide, silicon dioxide, alumina, aluminum, silver, yttrium, zirconium, titanium, and platinum.

Item 12. The plasma treatment detection indicator according to item 10 or 11, wherein the non-color-changing layer and the color-changing layer are formed on the base material in sequence, the non-color-changing layer is formed on the principal surface of the base material, and the color hanging layer is formed on the principal surface of the non-color-changing layer.

Advantageous Effects of Invention

In the plasma treatment detection indicator of the present invention, a specific metal element in the form of the simple substance and/or an inorganic compound containing the metal element is used as a color-changing material to be contained in a color-changing layer. The color of the color-changing layer is chemically changed because the valence of the metal element is changed by plasma treatment. This suppresses the gasification of the color-changing layer or scattering of the fine debris of the color-changing layer caused by plasma treatment to such a degree as to not affect the electronic device properties. In addition, because the color-changing material comprises one or more inorganic components, the indicator exhibits heat resistance capable of resisting the process temperature applied in electronic device production.

The plasma treatment detection indicator of the present invention is particularly useful as a plasma treatment detection indicator for use in electronic device production equipment, which must be treated in a vacuum and high-temperature condition, as well as in a highly clean environment. Examples of electronic devices include semiconductors, light-emitting diodes (LED), laser diodes, power devices, solar batteries, liquid crystal displays, and organic EL displays.

DESCRIPTION OF EMBODIMENTS

Figure 1:
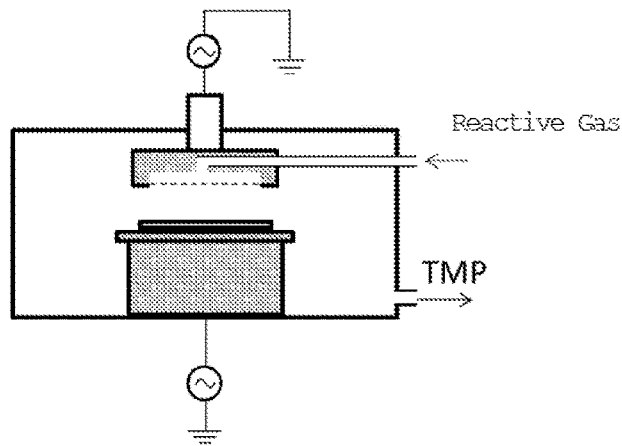
FIG. 1 is a schematic cross-sectional view of the CCP-type (CCP: capacitively coupled plasma) plasma etching apparatus used in Test Examples 1 and 3. The "TMP" in the figure is an abbreviation for turbo-molecular pump (the same applies to FIG. 2).

The following describes in detail the plasma treatment detection indicator according to the present invention.

The plasma treatment detection indicator according to the present invention (hereinafter, may be referred to as "the indicator of the present invention") comprises a color-changing layer that changes color by plasma treatment. The color-changing layer comprises at least one metal element selected from the group consisting of Mo, W, Sn, V, Ce, Te, and Bi in the form of a simple substance, and/or an inorganic compound containing at least one metal element selected from the group consisting of Mo, W, Sn, V, Ce, Te, and Bi.

In The plasma treatment detection indicator with this feature of the present invention, a specific metal element in the form of a simple substance and/or an inorganic compound containing the element is used as a color-changing material to be contained in a color-changing layer. The color of the color-changing layer is chemically changed because the valence of the metal element is changed by plasma treatment. This suppresses the gasification of the color-changing layer or scattering of the fine debris of the color-changing layer caused by plasma treatment to such a degree as to not affect the electronic device properties. In addition, because the color-changing material comprises one or more inorganic components, the indicator exhibits heat resistance capable of resisting the process temperature applied in electronic device production.

The indicator of the present invention is particularly useful as a plasma treatment detection indicator for use in electronic device production equipment, which must be treated in a vacuum and high-temperature condition, as well as in a highly clean environment. Examples of electronic devices include semiconductors, light-emitting diodes (LED), laser diodes, power devices, solar batteries, liquid crystal displays, and organic EL displays.

Color-Changing Layer

The indicator of the present invention comprises a color-changing layer that changes color by plasma treatment, and the color-changing layer comprises at least one metal element selected from the group consisting of Mo, W, Sn, V, Ce, Te, and Bi in the form of a simple substance and/or an inorganic compound containing at least one metal element selected from the group consisting of Mo, W, Sn, V, Ce, Te, and Bi. In particular, in the present invention, plasma treatment causes the valence of the at least one metal element to change, thus chemically changing the color. Unlike organic components, the gasification or the scattering of the fine debris of the at least one metal element in the form of a simple substance and the inorganic compound containing the at least one metal element caused by plasma treatment is suppressed to such a degree as to not affect the electronic device properties. In addition, the at least one metal element in the form of a simple substance and the inorganic compound containing the at least one metal element exhibit beat resistance capable of resisting the process temperature applied in electronic device production.

It is sufficient if the metal element is at least one member of Mo, W, Sn, V, Ce, Te, and Bi. Examples of the inorganic compound include at least one member selected from the group consistinq of oxides, hydroxides, carbonates, oxide salts, oxoacids, oxoacid salts, and oxo complexes of the metal element. The valence of the metal element of these inorganic compounds is preferably at least one member selected from the group consisting of Mo(II) to Mo(VI), W(II) to W(VI), Sn(II), Sn(IV), V(II) to V(V), Ce(III) to Ce(IV), Te(II), Te(IV), Te(VI), Bi(III), and Bi (V).

Specific examples of the inorganic compound include at least one member selected from the group consisting of molybdenum(IV) oxide, molybdenum(VI) oxide, tungsten (VI) oxide, tin(IV) oxide, vanadium(II) oxide, vanadium(III) oxide, vanadium(IV) oxide, vanadium(V) oxide, cerium(IV) oxide, tellurium(IV) oxide, bismuth(III) oxide, cerium(IV) hydroxide, bismuth (III) hydroxide, vanadium (III) hydroxide, molybdenum(V) hydroxide, bismuth (III) carbonate oxide, vanadium(IV) oxide sulfate., ammonium molybdate, sodium molybdate, potassium molybdate, sodium tungstate, ammonium tungstate, sodium orthovanadate, ammonium metavanadate, and sodium metavanadate.

Of these inorganic compounds, particularly preferable is at least one metal oxide selected from the group consisting of molybdenum(IV) oxide, molybdenum (VI) oxide, tungsten(VI) oxide, tin (IV) oxide, vanadium(II) oxide, vanadium(III) oxide, vanadium(IV) oxide, vanadium(V) oxide, cerium (IV) oxide, tellurium(IV) oxide, bismuth(III) oxide, cerium(IV) hydroxide, bismuth(III) hydroxide, vanadium (III) hydroxide, molybdenum(V) hydroxide, bismuth (III) carbonate oxide, and vanadium(IV) oxide sulfate. As the oxide, these containing a slight amount of crystalline water in their molecules are acceptable, but those containing no crystalline water may be preferable to exclude the possibility of releasing water molecules (moisture gas).

Of the metal oxides described above, preferable is at least one member of molybdenum(VI) oxide, tungsten(VI) oxide, vanadium (III) oxide, vanadium (V) oxide, and bismuth(III) oxide.

The color-changing layer of the indicator of the present invention comprises the metal element in the form of a simple substance and/or the inorganic compound containing the metal element (hereinafter, these may collectively be referred to as "the inorganic powder of the present invention"). The color-changing layer is desirably formed substantially of the inorganic powder of the present invention, and it is preferred that the inorganic powder of the present invention is present but organic components and others are absent. The inorganic powder of the present invention is contained in the form of a sintered object, a calcined object, aggregates (dry matter), and the like, as illustrated below.

Although the method for forming a color-changing layer is not limited, in embodiment 1, for example, a color-changing layer can be formed by molding the inorganic powder of the present invention (or its starting material powder) into pellets by a press machine, and sintering the pellets in an electric furnace. In embodiment 2, a color-changing layer can be formed by preparing a slurry containing the inorganic powder of the present invention (or its starting material powder), applying the slurry onto a substrate, evaporating the solvent, and calcining the substrate in the atmosphere. Additionally, in embodiment 3, a color-changing layer can be formed by preparing a slurry containing the inorganic powder of the present invention, applying the slurry onto a substrate, evaporating the solvent, and drying the substrate in the atmosphere.

The starting material powder for the inorganic powder of the present invention means a powder that is converted into the inorganic powder of the present invention by calcination. The starting material powder include hydroxides, carbonates, acetylacetonato complexes, oxide salts, oxoacids, oxoacid salts, and oxo complexes, each containing the metal element (at least one member of Mo, W, Sn, V, Ce, Te, and Bi). The oxoacids include not only ortho acids and meta acids, but also condensed oxoacids, such as isopoly acids and heteropoly acids.

Specifically, the starting material powder for the inorganic powder of the present invention includes vanadium(III) acetylacetonate, bismuth (III) nitrate, bismuth (III) hydroxide, bismuth (III) hydroxide nitrate, bismuth (III) carbonate oxide, bismuth(III) acetate oxide, bismuth(III) sulfate, bismuth(III) chloride, hexaammonium heptamolybdate tetrahydrate, ammonium tungstate para pentahydrate, ammonium vanadate(V), molybdenum dioxide acetonato, tungstic acid, molybdic acid, isopolytungstic acid, isopolymolybdic acid, and isopolyvanadium acid. These starting material powders in the present invention are converted into the inorganic powder of the present invention by calcination in embodiment 1 or embodiment 2. However, depending on the calcination conditions, there may be a case in which they are not completely converted into the inorganic powder of the present invention. Thus, it is acceptable if, depending on the calcination conditions, a slight amount of an unreacted component or organic component remains in the inorganic powder of the present invention to the degree that the remains do not affect the effect of the present invention.

In embodiment 1 (molding+sintering), a color-changing layer may be formed in accordance with an ordinary method for forming a ceramic sintered object, and in embodiments 2 and 3 (slurry application+calcination drying), the layer may be formed in accordance with an ordinary method in the related art. As a method for forming a coating film of a slurry in embodiments 2 and 3 a wide range of known printing methods and coating methods are usable. These methods include, for example, spin coating, slit coating, spray, dip coating, silk-screen printing, gravure printing, offset printing, relief printing, and flexographic printing.

Embodiment 1 is suitable for forming a color-changing layer typically having a thickness of about 1 to 4 mm. Embodiments 2 and 3 are suitable for forming a color-changing layer typically having a thickness of about 10 nm to 1 mm. In addition, when embodiment 2 or 3 is applied, the substrate on which a coating film of a slurry containing the inorganic powder of the present invention or its starting material powder is formed can also be used as a base material of the indicator of the present invention described later (base material for supporting the color-changing layer).

The thickness of the color-changing layer of the indicator of the present invention is not limited. However, it is preferably about 500 nm to 2 mm, and more preferably about 1 to 100 μm.

Base Material That Supports Color-Changing Layer

The indicator of the present invention may comprise a base material that supports the color-changing layer.

Any base material that allows the color-changing layer to form thereon and that supports the layer can be used. Examples of usable base materials include metals or alloys, ceramic, quartz, concrete, plastics (e.g., polyethylene terephthalate (PET), polytetrafluoroethylene (PTFE), polyether ether ketone (PEEK), polypropylene, nylon, polystyrene, polysulfone, polycarbonate, and polyimide), fabrics (non-woven fabrics, woven fabrics, glass fiber filters, and other fiber sheets), and composite materials thereof. Those typically known as an electronic device substrate, such as silicon, gallium arsenide, silicon carbide, sapphire, glass, gallium nitride, and germanium, can also be used as a base material of the indicator of the present invention. The thickness of the base material can suitably be determined in accordance with the type of the indicator.

Non-Color-Changing Layer

To enhance the visibility of the color-changing layer, the indicator of the present invention may be provided with, as an underlayer, a non-color-changing layer that does not change color by plasma treatment. The non-color-changing layer is required to not be gasified, as well as be heat resistant. The non-color-changing layer is preferably a white layer, a metal layer, and the like.

The white layer can be formed of, for example, titanium (IV) oxide, zirconium(IV) oxide, yttrium(III) oxide, barium sulfate, magnesium oxide, silicon dioxide, or alumina.

The metal layer can be formed of, for example, aluminum, silver, yttrium, zirconium, titanium, or platinum.

Examples of the method for forming a non-color-changing layer include physical vapor deposition (PVD), chemical vapor deposition (CVD), and sputtering. The layer can also be formed by preparing a slurry containing a substance to form a non-color-changing layer, applying the slurry onto a substrate, evaporating the solvent, and calcining the substrate in the atmosphere. Examples of slurry application and printing methods include a wide range of known coating methods and printing methods, such as spin coating, slit coating, spray coating, dip coating, silk-screen printing, gravure printing, offset printing, relief printing, and flexographic printing. The thickness of the: non-color changing layer can suitably be determined in accordance with the type of the indicator.

In the present invention, any combination of the color-changing layer and the non-color-changing layer is usable, as long as the completion of the plasma treatment is confirmed. For example, the color-changing layer and the non-color-changing layer can be formed such that the color change of the color-changing layer enables the first identification of color difference between the color changing layer and the non-color-changing layer, or such that the color change eliminates, for the first time, the difference in color between the color-changing layer and the non-color-changing layer. In the present invention, it is preferable to form a color-changing layer and a non-color-changing layer particularly such that the color change enables the first identification of color difference between the color-changing layer and the non-color-changing layer.

To enable the identification of color difference, a color-changing layer and a non-color-changing layer may be formed, for example, such that at least one of characters, patterns, and symbols appears because of the change in color of the color-changing layer. In the present invention, characters, patterns, and symbols include any information that signals change in color. These characters, etc., may be suitably designed in accordance with the intended use or other purposes.

The color-changing layer and the non-color-changing layer before color change may have different colors. Both of the color-changing layer and the non-color-changing layer may have, for example, substantially the same color, and color difference (contrast) between the layers may be identified for the first time after color change.

In the present invention, examples of preferable embodiments of the layered structure include (i) an indicator in which the color-changing layer is formed adjacent to at least one principal surface of a base material; and ii) an indicator in which the non-color-changing layer and the color-changing layer are formed in sequence on a base material, the non-color-changing layer formed adjacent to the principal surface of the base material and the color-changing layer formed adjacent to the principal surface of the non-color-changing layer.

Shape of the Indicator of the Present Invention

The shape of the indicator of the present invention is not particularly limited, and a wide range of shapes adopted for known plasma treatment detection indicators can be used. When the shape of the indicator of the present invention is made identical to the shape of the electronic device substrate used in electronic device production equipment, it becomes possible to easily detect whether plasma treatment is homogeneously performed on the entire electronic device substrate using the indicator as a "dummy substrate."

As used herein, the phrase "the shape of the indicator of the present invention is made identical to the shape of the electronic device substrate, used in electronic device production equipment" includes both of the following meanings: (i) the shape of the indicator is completely the same as the shape of the electronic device substrate used in electronic device production equipment; and (ii) the shape of the indicator is substantially the same as the shape of the electronic device substrate used in electronic device production equipment to the degree that the indicator can be placed (set) in the setting position on the electronic device substrate in the electronic device production equipment that performs plasma treatment.

The phrase "substantially the same" in meaning (ii) above includes, for example, the following meaning: the difference in length between the principal surface of the electronic device substrate (when the shape of the principal surface of the substrate is circular, the diameter; when the shape of the principal surface of the substrate is square, rectangular, or the like, the length and width) and the principal surface of the indicator of the present invention is within ±5.0 mm; and the difference in thickness between the electronic device substrate and the indicator of the present invention is within about ±1000 μm.

The indicator of the present invention is not limited to the use in electronic device production equipment. However, when used in electronic device production equipment, the indicator is preferably used in electronic device production equipment that performs at least one step selected from the group consisting of film-forming step, etching step, asking step, impurity-adding step, and washing step by plasma treatment.

Plasma

The plasma is not particularly limited, and plasma generated with a plasma-generating gas can be used. Of plasma, preferable is plasma that is generated with at least one plasma-generating gas selected from the group consisting of oxygen, nitrogen, hydrogen, chlorine, argon, silane, ammonia, sulfur bromide, boron trichloride, hydrogen bromide, water vapor, nitrous oxide, tetraethoxysilane, nitrogen trifluoride, carbon tetrafluoride, perfluoro cyclobutane, difluoromethane, trifluoromethane, carbon tetrachloride, silicon tetrachloride, sulfur hexafluoride, hexafluoroethane, titanium tetrachloride, dichlorosilane, trimethylgallium, trimethylindium, and trimethylaluminum. Of these plasma generating gases, particularly preferable is at least one member selected from the group consisting of carbon tetrafluoride, perfluoro cyclobutane, trifluoromethane, sulfur hexafluoride and a mixed gas of argon and oxygen.

Plasma can be generated with a plasma treatment apparatus (an apparatus for per plasma treatment by applying alternating-current power, direct-current power, pulse power, high-frequency power, microwave power, or the like in an atmosphere containing a plasma-generating gas to generate plasma). Particularly in electronic device production equipment, plasma treatment is used in a film-forming step, etching step, ashing step, impurity-adding step, washing step, and the like described later.

In a film-forming step, for example, a film can be grown on a semiconductor wafer at a low temperature of 400° C. or less at a relatively high growth rate by using both plasma and thermal energy in plasma CVD (chemical vapor deposition). Specifically, a material gas is introduced into a depressurized reaction chamber, and the gas is radical ionized by plasma excitation to allow a reaction. Plasma CVD include capacitively coupled plasma (anodic bonding-type or parallel plate-type), inductively coupled plasma, and ECR (electron cyclotron resonance) plasma.

Another film-forming step is a step by sputtering. A specific example is that when tens to thousands of voltage is applied between a semiconductor wafer and a target in an inert gas of about 1 Torr to $10^{-4}$ Torr (e.g., Ar) in a high-frequency discharge sputtering apparatus, ionized Ar is accelerated toward the target and collides with the target; this causes the target substance to be sputtered and deposit on the semiconductor wafer. At this stage, high-energy Y⁻ electrons are generated from the target at the same time. When colliding with. Ar atoms, the Y elections ionize Ar atoms (Ar⁺), thereby maintaining plasma.

Another film-forming step is a step by ion plating. A specific example is that the inside is made a high-vacuum condition of about $10^{-5}$ Torr to $10^{-7}$ Torr, and then an inert gas (e.g., Ar) or a reactive gas (e.g., nitrogen and hydrocarbon) is injected thereinto. Then, from the thermionic cathode (electron gun) of a processing apparatus, an electron beam is discharged toward the deposition material to generate plasma in which ions and electrons are separately present. Subsequently, a metal is heated and vaporized at a high temperature by an electron beam, and the vaporized metal particles are subjected to a positive voltage, allowing the electrons and the metal particles to collide in plasma. This causes the metal particles to become positive ions, which proceed toward the object to be processed; at the same time, the metal particles bind to a reactive gas, to promote a chemical reaction. The particles, of which a chemical reaction has been promoted, are accelerated toward the object to be processed to which negative electrons have been added, collide with the object with high energy, and are thereby deposited as a metal compound on the surface. A vapor deposition method similar to ion plating is also an example of the film-forming step.

In addition, the oxidizing and nitriding step includes a method for converting the semiconductor wafer surface into an oxide film by plasma oxidation using, for example, ECR plasma or surface wave plasma; and a method for converting the semiconductor wafer surface into a nitride film by introducing an ammonia gas, and dissociating, decomposing, and ionizing the ammonia gas by plasma excitation.

In the etching step, for example, in a reactivity ion etching apparatus (RIE), circular plate electrodes are placed in parallel, and a reaction gas is introduced into a depressurized reaction chamber (chamber). The introduced reaction gas is then radicalized or ionized by plasma excitation such that the radicals or ions are present between the electrodes. The etching step uses effects of both etching that causes a substance on the semiconductor wafer to volatize by using a chemical reaction between these radicals or ions and the material; and physical sputtering. As a plasma etching apparatus, a barrel-type (cylindrical) etching apparatus, as well as the parallel plate-type etching apparatus, can be used.

Another etching step is reverse sputtering. Reverse sputtering is similar in principle to sputtering. Reverse sputtering is an etching method in which ionized Ar in plasma is allowed to collide with the semiconductor wafer. Ion beam etching, similar to reverse sputtering, is also an example of the etching step.

In the ashing step, for example, a photoresist is decomposed and volatilized using oxygen plasma obtained by plasma excitation of oxygen gas under reduced pressure.

In the impurity-adding step, for example, a gas containing impurity atoms for doping is introduced into a depressurized chamber, and plasma is excited to ionize the impurities. A negative bias voltage is applied to the semiconductor wafer to dope the wafer with the impurity ions.

The washing step is a step for removing foreign materials adhered to the semiconductor wafer without causing damage to the wafer before performing each step on the wafer. Examples include plasma washing that causes a chemical reaction with oxygen gas plasma, and plasma washing (reverse sputtering) that physically removes foreign materials by inert gas (e.g., argon) plasma.

EXAMPLES

The following describes the present invention in detail by showing Examples and Comparative Examples. However, the present invention is not limited to the Examples.

Examples 1 to 5

Preparation of Indicator Consisting of Color-Changing Layer in Pellet Form

The following were prepared for use i the Examples as inorganic powders of the present invention (metal oxide powder).

Example 1: $MoO_3$ powder (Wako Pure Chemical Industries, Ltd., mean particle size: 60 µm, 0.3 g)
Example 2: $WO_3$ powder (Wake Pure Chemical industries, Ltd., mean particle size: 60 µm, 0.3 g)
Example 3: $V_2O_3$ powder (Wako Pure Chemical Industries, Ltd., mean particle size: 60 µm, 0.3 g)
Example 4: $V_2O_5$ (Wako Pure Chemical Industries, Ltd., mean particle size: 60 µm, 0.3 g)
Example 5: $Bi_2O_3$ powder (Wake Pure Chemical Industries, Ltd., mean particle size: 60 µm, 0.3 g)

Each metal oxide powder was molded into a pellet form with a press machine, and then sintered in an electric furnace (600° C., 1 hour), thereby preparing an indicator consisting of a color-changing layer in pellet form ($\phi$=7 mm, t=2 mm).

Example 6

Preparation of Indicator Formed by Depositing a Thin Color-Changing Layer on a Base Material A slurry of the formulation shown in Table 1 below was prepared, and applied on a quartz substrate and calcined, thereby forming a 500-nm $Bi_2O_3$ thin film on the substrate.

TABLE 1

| Name of Substance | wt % |
| --- | --- |
| Bismuth(III) Oxide | 5 |
| Turpentine Oil | 45 |
| N-butyl Acetate | 22 |
| Ethyl Acetate | 8 |
| Stabilizer | 20 |
| Total | 100 |

Specifically, the slurry containing $Bi_2O_3$ of the formulation shown above was spin coated (2000 rpm, 20 sec.) on a 4-inch Si wafer, which is a substrate, and then the coated film was dried in the atmosphere at 120° C. for 10 minutes, followed by calcination of the coating film in the atmosphere at 550° C. for 10 minutes, thereby forming a $Bi_2O_3$ thin film.

This prepared an indicator having a thin color-changing layer deposited on the base material.

Test Example 1

FIG. 1 is a schematic cross-sectional view of a CCP-type (CCP: capacitively coupled plasma) plasma etching apparatus.

The apparatus is provided with parallel-plate electrodes inside the vacuum vessel, and the upper electrode has a shower structure, by which a reactive gas is supplied to the surface of the object to be treated in a shower-like manner. The lower electrode is provided with a high-frequency power-feeding mechanism for plasma excitation and a cooling mechanism through which a cooling medium for cooling the object to be treated can circulate.

When etching is actually performed, the vacuum vessel is degassed, and then a reactive gas is introduced from the shower part of the upper electrode. High-frequency power supplied from the upper electrode generates plasma in the space of the parallel-plate electrodes, and the generated excited species cause a chemical reaction, which performs etching on the surface of the object to be treated.

In Test Example 1, the indicators prepared in Examples 1 to 5 were placed in this apparatus, carbon tetrafluoride gas ($CF_4$) as a reactive gas was introduced thereinto, and plasma treatment was performed. The color change of the color-changing layer of each indicator was evaluated.

Table 2 shows the plasma treatment conditions.

TABLE 2

| Gas Flow (ccm) | Pressure (Pa) | High-frequency Power (W) | Treatment Time (min.) |
| --- | --- | --- | --- |
| 5 | 40 | 75 | 10 |

Table 3 shows the results of color change evaluation of the color-changing layer of each indicator.

TABLE 3

| Chemical Formula | Results of Color Change |
| --- | --- |
| $MoO_3$ | White -> Pale Blue |
| $WO_3$ | Pale Yellow -> Pale Blue |
| $V_2O_3$ | Orange -> Light Green |
| $V_2O_5$ | Orange -> Light Green |
| $Bi_2O_3$ | Pale Yellow -> Brown |

As is clear from the results shown in Table 3, the color-changing layer of each indicator of Examples 1 to 5 changed color by plasma treatment. The metal oxides used in Examples 1 to 5 are known to exhibit different colors depending on the difference in the valence of the metal element, and it is speculated that the plasma treatment changed the valence of the metal oxides, which led to color change.

Test Example 2

Figure 2:
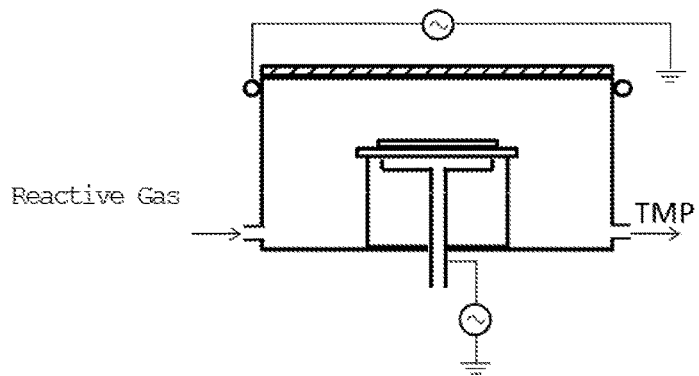
FIG. 2 is a schematic cross-sectional view of the ICP-type (ICP: inductively coupled plasma) plasma etching apparatus used in Test Example 2.

FIG. 2 is a schematic cross-sectional view of an ICP-type (ICP: inductively coupled plasma) plasma etching apparatus.

The apparatus is provided with a chamber capable of evacuating the inside and a stage on which a wafer, which is an object to be treated, is placed. The chamber is provided with a gas inlet from which a reactive gas is introduced, and an exhaust outlet for evacuating the chamber. The stage is provided with an electrostatic adsorption power source for electrostatically adsorbing a wafer, and a cooling mechanism through which a cooling medium for cooling circulates. A coil for plasma excitation and a high-frequency power source as an upper electrode are provided above the chamber.

When etching is actually performed, a wafer is delivered from a wafer inlet into the chamber, and electrostatically adsorbed onto the stage by the electrostatic adsorption power source. Subsequently, a reactive gas is introduced into the chamber. The chamber is depressurized and evacuated with a vacuum pump, and adjusted to a predetermined pressure. Subsequently, high-frequency power is applied to the upper electrode to excite the reactive gas, thereby generating plasma in the space above the wafer. Alternatively, bias may be applied by the high-frequency power source connected to the stage. When the latter is the case, ions in plasma enter the wafer in an accelerated manner. The action of the generated plasma excited species etches the surface of the wafer. During the plasma treatment, helium gas flows through the cooling mechanism provided to the stage, thus cooling the wafer.

In Test Example 2, the indicators prepared in Examples 1 to 5 were placed in this apparatus, and carbon tetrafluoride gas ($CF_4$), sulfur hexafluoride gas ($SF_6$), perfluoro cyclobutane gas ($C_4F_8$), trifluoromethane gas ($CHF_3$), oxygen ($O_2$), argon (Ar), chlorine ($Cl_2$), or hydrogen ($H_2$) was individually introduced as a reactive gas to perform plasma treatment. The color change of the color-changing layer of each indicator was evaluated.

Table 4 shows the plasma treatment conditions.

TABLE 4

| Condition No. | Gas Flow Rate (sccm) | | | | | | | | Pressure (Pa) | ICP (W) | Treatment Time (min.) |
|---|---|---|---|---|---|---|---|---|---|---|---|
| | $CF_4$ | $SF_6$ | $C_4F_6$ | $CHF_3$ | $O_2$ | Ar | $Cl_2$ | $H_2$ | | | |
| 1 | 30 | | | | | | | | 2.00 | 500 | 10 |
| 2 | | 50 | | | | | | | 1.00 | 300 | 10 |
| 3 | | | 85 | | | | | | 2.66 | 600 | 10 |
| 4 | | | | 30 | | | | | 2.00 | 500 | 10 |
| 5 | | | | | 100 | | | | 10.00 | 500 | 10 |
| 6 | | | | | | 50 | 25 | | 7.50 | 600 | 10 |
| 7 | | | | | | | 50 | | 5.00 | 800 | 10 |
| 8 | | | | | | | 50 | | 1.00 | 200 | 10 |
| 9 | | | | | | | | 100 | 2.00 | 400 | 10 |

Table 5 shows the results of the color change evaluation of the color-changing layer of each indicator.

TABLE 5

| Chemical Formula | Treatment Condition No. | | | | | | | | |
|---|---|---|---|---|---|---|---|---|---|
| | No. 1 | No. 2 | No. 3 | No. 4 | No. 5 | No. 6 | No. 7 | No. 8 | No. 9 |
| $MoO_3$ | — | — | ✓ | ✓ | — | — | — | — | ✓ |
| $WO_3$ | — | — | ✓ | ✓ | — | — | — | — | ✓ |
| $V_2O_3$ | — | — | ✓ | ✓ | — | — | — | — | ✓ |
| $V_2O_5$ | — | — | ✓ | ✓ | — | — | — | — | ✓ |
| $Bi_2O_3$ | ✓ | ✓ | ✓ | ✓ | ✓ | ✓ | ✓ | ✓ | ✓ |

In the table, "✓" denotes that color change occurred, and "—" denotes that color Change did not occur.

Test Example 3

The indicator prepared in Example 6 placed in the plasma etching apparatus used in Test Example 1, and carbon tetrafluoride gas ($CF_4$) was introduced as a reactive gas thereinto to perform plasma treatment. The color change of the color-changing layer of the indicator was evaluated.

Table 6 shows the plasma treatment conditions.

TABLE 6

| Gas Flow (ccm) | Pressure (Pa) | High-frequency Power (W) | Treatment Time (min.) |
|---|---|---|---|
| 5 | 40 | 75 | 10 |

After the plasma treatment, the color was changed from pale yellow to brown as in Test Example 1. This confirms that $Bi_2O_3$ can change color, even in the form of a thin film.

Test Example 4

The indicator prepared in Example 5 and a plasma treatment detection indicator containing organic components in its color-changing layer according to prior art 1 were prepared, and their outgassing characteristic when the temperature was increased were compared. The plasma treatment detection indicator of prior art 1 had a color-changing layer formed on a base material; the color-changing layer was formed by applying an ink composition of the formulation shown in Table 7 below (the components are all organic components), and drying the coated film.

TABLE 7

| Name of Substance | wt % |
|---|---|
| Color-changing Colorant | 0.1 |
| Non-color-changing Colorant | 2 |
| Stabilizer | 4 |
| Thickener | 12 |
| Binder Resin | 10 |
| Solvent | 71.9 |
| Total | 100 |

Figure 3:
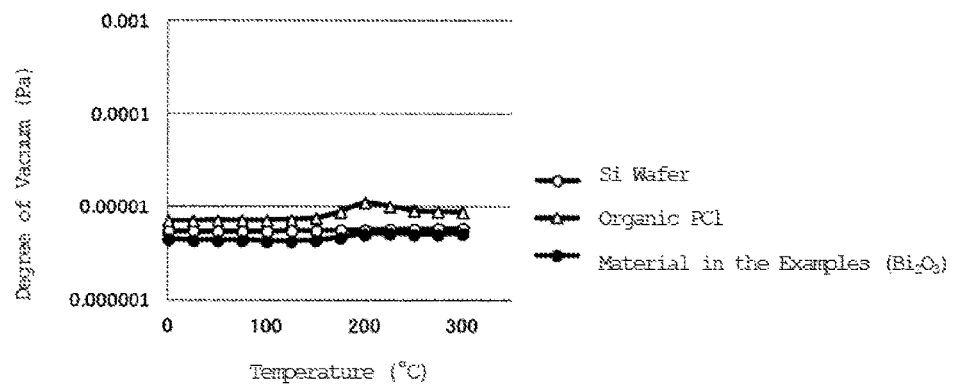
FIG. 3 shows the results of Test Example 4 (outgassing characteristics at the time of temperature increase).

Specifically, the indicator of Example 5 and the indicator of prior art 1 were individually mounted on a stage whose temperature can be increased, and individually placed in a vacuum apparatus. After the, inside, of the apparatus was evacuated to achieve a degree of vacuum of 1.0 E-6 Pa, the outgassing characteristics were studied based on the change in the degree of vacuum inside the vacuum apparatus while the temperature of the stage was raised at 30° C./min. FIG. 3 shows the results of the outgassing characteristics.

As is clear from results shown in FIG. 3, while the indicator of prior art 1 exhibited a great change in the degree of vacuum over the temperature of 150° C. to 200° C., the indicator of Example 5 exhibited less change in the degree of vacuum than the indicator of prior art 1. This reveals that the indicator containing an inorganic substance as a color-changing material according to the present invention releases less gas than the indicator containing organic components in its color-changing layer according to prior art 1.

After the temperature was increased, the color of each sample was observed. The observation results reveal that while the indicator of prior art 1 changed color because of heat, the indicator of Example 5 did not exhibit a color change because of heat.

The probable reason for this is that because the indicator of prior art 1 contained organic components in the color-changing layer, the organic components decomposed at a temperature of around 200° C., accompanied by gas release and color change of the color-changing colorant; however, the indicator prepared in Example 5 contained an inorganic component, which has a relatively higher decomposition temperature than organic components, thus exhibiting excellent outgassing characteristics and heat resistance.

The invention claimed is:

1. A plasma treatment detection indicator comprising a color-changing layer that changes color by plasma treatment,
    wherein the color-changing layer comprises an inorganic powder,
    wherein the inorganic powder is formed from at least one metal element selected from the group consisting of Mo, W, Sn, V, Ce, Te, and Bi in the form of a simple substance and/or the inorganic powder is formed from an inorganic compound containing at least one metal element selected from the group consisting of Mo, W, Sn, V, Ce, Te, and Bi,
    wherein the color-changing layer does not include organic components other than the inorganic powder; and
    wherein the valence of the metal element is configured to be changed by the plasma treatment.

2. The plasma treatment detection indicator according to claim 1, wherein the valence of at least one metal element contained in the inorganic compound is at least one member selected from the group consisting of Mo(II) to Mo(VI), W(II) to W(VI), Sn(II), Sn(IV), V(II) to V(V), Ce(III) to Ce(IV), Te(II), Te(IV), Te(VI), Bi(III), and Bi (V).

3. The plasma treatment detection indicator according to claim 1, wherein the inorganic compound is at least one member selected from the group consisting of oxides, hydroxides, carbonates, oxide salts, oxoacids, oxoacid salts, and oxo complexes of the at least one metal element.

4. The plasma treatment detection indicator according to claim 1, wherein the color-changing layer comprises at least one member selected from the group consisting of molybdenum(IV) oxide, molybdenum(VI) oxide, tungsten(VI) oxide, tin(IV) oxide, vanadium(II) oxide, vanadium(III) oxide, vanadium(IV) oxide, vanadium(V) oxide, cerium(IV) oxide, tellurium(IV) oxide, bismuth(III) oxide, cerium(IV) hydroxide, bismuth(III) hydroxide, vanadium(III) hydroxide, molybdenum(V) hydroxide, bismuth(III) carbonate oxide, vanadium(IV) oxide sulfate, ammonium molybdate, sodium molybdate, potassium molybdate, sodium tungstate, ammonium tungstate, sodium orthovanadate, ammonium metavanadate, and sodium metavanadate.

5. The plasma treatment detection indicator according to claim 1, wherein the color-changing layer comprises at least one member selected from the group consisting of molybdenum(VI) oxide, tungsten(VI) oxide, vanadium(III) oxide, vanadium(V) oxide, and bismuth(III) oxide.

6. The plasma treatment detection indicator according to claim 1, comprising a base material that supports the color-changing layer.

7. The plasma treatment detection indicator according to claim 1, which is an indicator for use in electronic device production equipment.

8. The plasma treatment detection indicator according to claim 7, wherein the shape of the indicator is identical to the shape of an electronic device substrate for use in the electronic device production equipment.

9. The plasma treatment detection indicator according to claim 7, wherein the electronic device production equipment performs at least one plasma treatment selected from the group consisting of film-forming step, etching step, ashing step, impurity-adding step, and washing step.

10. The plasma treatment detection indicator according to claim 1, comprising a non-color-changing layer that does not change color by plasma treatment.

11. The plasma treatment detection indicator according to claim 10, wherein the non-color-changing layer comprises at least one member selected from the group consisting of titanium(IV) oxide, zirconium(IV) oxide, yttrium(III) oxide, barium sulfate, magnesium oxide, silicon dioxide, alumina, aluminum, silver, yttrium, zirconium, titanium, and platinum.

12. The plasma treatment detection indicator according to claim 10, wherein the non-color-changing layer and the color-changing layer are formed on the base material in sequence,
    the non-color-changing layer is formed on the principal surface of the base material, and the color-changing layer is formed on the principal surface of the non-color-changing layer.

* * * * *